US005508136A

United States Patent [19]
Shirota et al.

[11] Patent Number: 5,508,136
[45] Date of Patent: Apr. 16, 1996

[54] TRISARYLAMINOBENZENE DERIVATIVES, COMPOUNDS FOR ORGANIC EL ELEMENT, AND ORGANIC EL ELEMENT

[75] Inventors: Yasuhiko Shirota, 5-7, Daikoku-cho 3-chome, Toyonaka-shi, Osaka-fu; Kenji Nakaya, Chiba; Tetsushi Inoue, Chiba; Norihiro Okada, Chiba; Kenryo Namba, Tokyo, all of Japan

[73] Assignees: Yasuhiko Shirota, Toyonaka; TDK Corporation, Tokyo, both of Japan

[21] Appl. No.: 194,145

[22] Filed: Feb. 10, 1994

[30] Foreign Application Priority Data

Feb. 10, 1993 [JP] Japan ................................. 5-045785
May 19, 1993 [JP] Japan ................................. 5-140041

[51] Int. Cl.$^6$ ........................ G03G 5/04; C07L 211/54
[52] U.S. Cl. ................................. 430/73; 564/434
[58] Field of Search ........................ 564/434; 430/73; 428/690, 917

[56] References Cited

U.S. PATENT DOCUMENTS

| | | | |
|---|---|---|---|
| 3,234,280 | 2/1966 | Fox et al. ................................. | 430/73 |
| 3,966,468 | 6/1976 | Contois et al. ........................... | 430/73 |
| 4,299,897 | 10/1981 | Stolka et al. ............................. | 430/73 |
| 4,720,432 | 1/1988 | Van Slyke .................................. | 428/457 |
| 4,769,292 | 9/1988 | Tang et al. ................................. | 428/690 |
| 4,788,336 | 11/1988 | Rule ......................................... | 430/73 |
| 4,920,022 | 4/1990 | Sakakubara et al. ..................... | 430/73 |
| 5,342,719 | 8/1994 | Pai et al. ................................... | 430/73 |

FOREIGN PATENT DOCUMENTS

| | | |
|---|---|---|
| 0455247 | 11/1991 | European Pat. Off. . |
| 0508562 | 10/1992 | European Pat. Off. . |
| 3287862 | 11/1988 | Japan . |
| 1154571 | 6/1989 | Japan . |
| 1217357 | 8/1989 | Japan . |
| 1224353 | 9/1989 | Japan . |
| 2191694 | 7/1990 | Japan . |
| 3-792 | 1/1991 | Japan . |
| 4308688 | 10/1992 | Japan . |

OTHER PUBLICATIONS

Chemical Abstracts, vol. 118, No. 10, Mar. 8, 1993, AN 90870r & JP-A-4290851, Oct. 15, 1992.
Chemical Abstracts, vol. 118, No. 3, Jan. 18, 1993, AN 22141d & JP 4178367, Jun. 25, 1992.
Advanced Materials, vol. 5, No. 7/8, Jul. 5, 1993, Wataru Ishikawa, et al., pp. 559–561, "Novel Amorphous Molecular Materials: The Starburst Molecule 1,3,5-tris [N-(4-Diphenyl-Aminophenyl)Phenylamino]benzene".
J. Phys. D: Appl. Phys., vol. 26, 1993, pp. 1394–1397, E N Gulamov, et al., "Anodic Oxide Film Influence on Formation of Anode Spots and Glow Discharge Stability".
J. Phys. D: Appl. Phys., vol. 26, 1993, pp. 894–899, Wataru Ishikawa, et al., "Polymorphism of Starburst Molecules: Methyl–Substituted Derivatives of 1,3,5-Tris(Diphenylamino)Benzene".
Mol. Cryst. Liq. Cryst., 1992, vol. 211, pp. 431–438, Wataru Ishikawa, et al., "Starburst Molecules for Amorphous Molecular Materials: Synthesis and Morphology of 1,3, 5–Tris(Diphenylamino)Benzene and Its Methyl–Substituted Derivatives".
Chemistry Letters, 1991, pp. 1731–1734, Wataru Ishikawa, et al., "Methyl–Substituted Derivatives of 1,3,5-Tris(Diphenylamino)Benzene as a Novel Class of Amorphous Molecular Materials".
The Japanese Chemical Society's 63rd Spring Meeting in 1992, Y. Shirota, "Amorphous Molecular Materials", pp. 2571–2574.
The Japanese Chemical Society's 61st Spring Meeting in 1991, 3 D3 36, 3 D3 37, 3 D3 38, 4 F8 18, 4 F8 25, 4 F8 26, and 4 F8 32, 5 pages.
Polymer Preprints, Japan, vol. 41, No. 3, 1992, K. Nawa, et al., "Synthesis and Properties of a Novel Non-Conjugated Polymer Containing Pendant Oligothiophene Groups", p. 585.

Primary Examiner—Richard L. Raymond
Assistant Examiner—Deborah Lambkin
Attorney, Agent, or Firm—Oblon, Spivak, McClelland, Maier, & Neustadt

[57] ABSTRACT

Novel trisarylaminobenzene derivatives are represented by the formula:

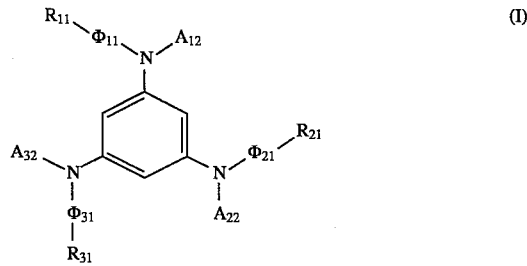

(I)

wherein $\Phi_{11}$, $\Phi_{21}$, and $\Phi_{31}$ are independently divalent aromatic ring residues, $R_{11}$, $R_{21}$, and $R_{31}$ are independently groups represented by —$N\Phi_{01}\Phi_{02}$, —$NH\Phi_{01}$, —$NR_{01}\Phi_{01}$, —$\Phi_{01}$, —$O\Phi_{01}$ or —$S\Phi_{01}$ wherein each of $\Phi_{01}$ and $\Phi_{02}$ is a monovalent aromatic ring residue, and $R_{01}$ is an alkyl group, at least one of $R_{11}$, $R_{21}$, and $R_{31}$ being a group represented by —$N\Phi_{01}\Phi_{02}$, —$NH\Phi_{01}$ or —$NR_{01}\Phi_{01}$, and $A_{12}$, $A_{22}$, and $A_{32}$ are independently aromatic residues, alkyl groups or hydrogen. An organic electroluminescent element which uses the compound in an organic compound layer, especially in a hole injection transport layer provides uniform plane light emission and is durable enough to maintain luminance.

10 Claims, 5 Drawing Sheets

TRISARYLAMINOBENZENE DERIVATIVES, COMPOUNDS FOR ORGANIC EL ELEMENT, AND ORGANIC EL ELEMENT

This invention relates to novel trisarylaminobenzene derivatives, compounds for organic electroluminescent elements, and organic electroluminescent elements.

BACKGROUND OF THE INVENTION

Organic electroluminescent (EL) elements include a thin film containing a luminescent organic compound interposed between a cathode and an anode. Electrons and holes are injected into a thin film where they are recombined to create excitons. Light is emitted by utilizing luminescence (phosphorescence or fluorescence) upon deactivation of excitons. The organic EL elements are characterized by plane light emission at a high luminance of about 1000 cd/m$^2$ with a low voltage of less than 10 volts and light emission in a spectrum from blue to red color by a simple choice of the type of fluorescent material.

The organic EL elements, however, are undesirably short in effective life, less durable and less reliable because of the following factors.

(1) Physical changes of organic compounds: To prevent dielectric breakdown of elements due to defects along grain boundaries and surface non-uniformity, an organic compound capable of forming a smooth amorphous thin film must be used. However, the film is less stable in quality and thus allows crystallization to take place with the lapse of time and such crystallization is promoted by a temperature rise of the element due to heat build-up during operation, resulting in a change of film quality. There is a need for a material which can be made vitreous by simple means such as vacuum evaporation and maintains the vitreous state in a stable manner.

(2) Oxidation and stripping of the cathode: Metals having a low work function such as Mg, Li and Na are used as the cathode in order to increase its electron injection efficiency while these metals are reactive with oxygen and moisture in air. As a result, the cathode can be stripped from the organic layer.

(3) Low emission efficacy and increased heat build-up: As the element temperature rises, crystallization is promoted and the organic layer can be melted and broken. It is desired to increase the conversion efficiency of input energy and to find a material capable of imparting heat resistance to the organic layer.

(4) Opto-chemical and electro-chemical changes of organic compounds.

Shirota who is one of the present inventors has made a number of proposals and reports about π-electron system amorphous molecular materials as disclosed in Japanese Patent Application Kokai (JP-A) No. 308688/1992, Polymer Preprints, Japan, Vol. 41, No. 3 (1992), the Japanese Chemical Society's 61st Spring Meeting in 1991, 3D3 36, 3D3 37, 3D3 38, 4F8 18, 4F8 25, 4F8 26, 4F8 32, and the Japanese Chemical Society's 63rd Spring Meeting in 1992, P2571–2574.

SUMMARY OF THE INVENTION

A primary object of the present invention is to provide a novel compound performing optical and electronic functions with minimized physical, opto-chemical and electro-chemical changes. Another object of the present invention is to provide an organic electroluminescent element utilizing the compound, featuring reliability, durability and high radiation emission efficacy.

According to a first aspect of the present invention, there is provided a trisarylaminobenzene derivative of the following formula:

(I)

wherein $\Phi_{11}$, $\Phi_{21}$, and $\Phi_{31}$ are independently divalent aromatic ring residues; $R_{11}$, $R_{21}$, and $R_{31}$ are independently selected from groups represented by —$N\Phi_{01}\Phi_{02}$, —$NH\Phi_{01}$, —$NR_{01}\Phi_{01}$, —$\Phi_{01}$, —$O\Phi_{01}$ and —$S\Phi_{01}$ wherein each of $\Phi_{01}$ and $\Phi_{02}$ is a monovalent aromatic ring residue, and $R_{01}$ is an alkyl group, at least one of $R_{11}$, $R_{21}$, and $R_{31}$ being a group represented by —$N\Phi_{01}\Phi_{02}$, —$NH\Phi_{01}$ or —$NR_{01}\Phi_{01}$; and $A_{12}$, $A_{22}$, and $A_{32}$ are independently monovalent aromatic residues, alkyl groups or hydrogen atoms.

Preferably, each of $R_{11}$, $R_{21}$, and $R_{31}$ is a group represented by —$N\Phi_{01}\Phi_{02}$, —$NH\Phi_{01}$ or —$NR_{01}\Phi_{01}$.

Trisarylaminobenzene derivatives of one preferred class are of the following formula:

(II)

wherein $\Phi_{11}$, $\Phi_{21}$, $\Phi_{31}$, $\Phi_{01}$, and $\Phi_{02}$ are as defined in formula (I), the three $\Phi_{01}$ groups may be identical or different and the three $\Phi_{02}$ groups may be identical or different, and $\Phi_{12}$, $\Phi_{22}$, and $\Phi_{32}$ are independently monovalent aromatic residues.

More preferred among the derivatives of the formula (II) are those of the following formula:

(III)

wherein $R_1$ and $R_2$ groups, nine in total, may be identical or different and each selected from the group consisting of a hydrogen atom, halogen atom, alkyl group, aryl group, alkoxy group, aryloxy group, aralkyl group, alkaryl group, primary to tertiary amino group, cyano group, and nitro group.

Trisarylaminobenzene derivatives of another preferred class are of the following formula:

(IV)

wherein $\Phi_{11}$, $\Phi_{21}$, $\Phi_{31}$, $\Phi_{01}$, and $\Phi_{02}$ are as defined in formula (I), the three $\Phi_{01}$ groups may be identical or different and the three $\Phi_{02}$ groups may be identical or different, and $R_{12}$, $R_{22}$, and $R_{32}$ are independently alkyl groups or hydrogen atoms.

More preferred among the derivatives of formula (IV) are those of the following formula:

(V)

wherein R groups, six in total, may be identical or different and each selected from the group consisting of a hydrogen atom, halogen atom, alkyl group, aryl group, alkoxy group, aryloxy group, aralkyl group, alkaryl group, primary to tertiary amino group, cyano group, and nitro group, and $R_{12}$, $R_{22}$, and $R_{32}$ are as defined in formula (IV).

Also contemplated herein is a compound for use in an organic electroluminescent element. It is a trisarylaminobenzene derivative as defined above.

Therefore the present invention also provides an organic electroluminescent (EL) element comprising a layer containing the compound. More particularly, the organic EL element is defined as comprising a hole injection transport layer, a light emitting layer, and optionally an electron injection transport layer wherein the inventive compound is contained in the hole injection transport layer.

ADVANTAGES

The trisarylaminobenzene derivatives of formula (I) are novel compounds having a high melting point and a high glass transition temperature (Tg). Thin films formed from these compounds as by evaporation are of quality in that they are transparent, have a smooth surface, and maintain a stable amorphous state at room temperature or higher. These advantages are derived from the following facts.

(1) The compound is increased in molecular weight so as to have a higher melting point.

(2) The molecule is increased in rigidity so as to exhibit a high glass transition temperature above room temperature.

(3) A bulky substituent providing steric hindrance such as a phenyl group is introduced to optimize intermolecular overlap.

(4) The number of conformations that the molecule can assume is increased to restrain rearrangement of the molecule.

(5) The molecular structure is non-planar.

Because of inclusion of many hole injection transport units such as N-phenyl groups in a molecule and a non-planar structure, it is unlikely that stable structural traps for holes such as dimer trap radical ions are formed between adjacent molecules. This leads to an improved hole injection transport ability.

Since the organic EL element of the invention uses a trisarylaminobenzene derivative of formula (I), typically a 1,3,5-trisdiarylaminobenzene derivative of formula (II) or 1,3,5-trismonoarylaminobenzene derivative of formula (IV) in an organic compound layer, preferably in a hole injection transport layer as an organic electroluminescent compound, the element ensures uniform plane light emission and maintains high luminance over a long period of time in a stable manner. The element maintains emission at a high luminance of at least about 100 $cd/m^2$, especially at least about 1000 $cd/m^2$ over a long period of time in a stable manner though the luminance depends on the wavelength of emitted radiation.

DETAILED DESCRIPTION OF THE INVENTION

The compounds of the present invention are tris(di- or mono-arylamino)benzene derivatives of formula (I) having a molecular weight above a predetermined level. In formula (I), each of the three divalent aromatic ring residues $\Phi_{11}$, $\Phi_{21}$, and $\Phi_{31}$ may have a fused ring and is any of divalent residues of aromatic hydrocarbon rings and aromatic heterocyclic rings, for example, benzene, naphthalene, anthracene, etc.; thiophene; furan; pyrrole; and biphenyl. Often these residues are identical although they may be different. The aromatic rings may have a substituent or substituents, for example, alkyl groups preferably having 1 to 8 carbon atoms, especially 1 to 6 carbon atoms, aryl groups preferably having 6 to 15 carbon atoms, alkoxy and aryloxy groups having said alkyl and aryl groups, aralkyl and alkaryl groups having said alkyl and aryl groups, primary to tertiary amino groups which may have said alkyl and aryl groups, cyano groups, nitro groups, and halogen atoms. Preferably $\Phi_{11}$, $\Phi_{21}$, and $\Phi_{31}$ are 1,4-phenylene groups which may have a substituent, more preferably unsubstituted 1,4-phenylene groups.

In formula (I), $R_{11}$, $R_{21}$, and $R_{31}$ are independently aromatic ring-containing groups selected from diarylamino groups —$N\Phi_{01}\Phi_{02}$, monoarylamino groups —$NH\Phi_{01}$, arylakylamino groups —$NR_{01}\Phi_{01}$, aryl groups —$\Phi_{01}$, aryloxy groups —$O\Phi_{01}$, and arylthio groups —$S\Phi_{01}$. The groups $\Phi_{01}$ and $\Phi_{02}$ may be identical or different and each is a monovalent aromatic hydrocarbon ring or aromatic heterocyclic residue which may have a substituent as mentioned above or a fused ring as mentioned above.

The aromatic residues represented by $\Phi_{01}$ and $\Phi_{02}$ may have a substituent or substituents, for example, alkyl groups preferably having 1 to 8 carbon atoms, especially 1 to 6 carbon atoms, aryl groups preferably having 6 to 15 carbon atoms, alkoxy and aryloxy groups having said alkyl and aryl groups, aralkyl and alkaryl groups having said alkyl and aryl groups, primary to tertiary amino groups which may have said alkyl and aryl groups, cyano groups, nitro groups, and halogen atoms. Preferred substituents are alkyl groups having 1 to 8 carbon atoms, more preferably 1 to 6 carbon atoms, most preferably 1 to 4 carbon atoms, and aryl groups. The alkyl groups may be either linear or branched. Phenyl is the preferred aryl group. The aryl group may have a substituent represented by —$N\Phi_{01}\Phi_{02}$, —$NH\Phi_{01}$ or —$NR_{01}\Phi_{01}$.

$R_{01}$ is preferably an alkyl group having 1 to 8 carbon atoms, more preferably 1 to 6 carbon atoms, most preferably 1 to 4 carbon atoms. The alkyl group may be either linear or branched. Although an unsubstituted alkyl group is preferred in most cases, the alkyl group may have a substituent or substituents, for example, alkyl groups preferably having 1 to 8 carbon atoms, aryl groups preferably having 6 to 15 carbon atoms, alkoxy and aryloxy groups having said alkyl and aryl groups, aralkyl and alkaryl groups having said alkyl and aryl groups, primary to tertiary amino groups which may have said alkyl and aryl groups, cyano groups, nitro groups, and halogen atoms.

In formula (I), there are included in total three $R_{11}$, $R_{21}$, and $R_{31}$ groups. At least one, preferably two or three, especially three of these groups are aromatic ring-containing groups —$N\Phi_{01}\Phi_{02}$, —$NH\Phi_{01}$ or —$NR_{01}\Phi_{01}$, especially diarylamino groups —$N\Phi_{01}\Phi_{02}$. Preferred —$N\Phi_{01}\Phi_{02}$ groups are —$NPh_2$ wherein Ph is a substituted or unsubstituted phenylene groups.

In formula (I), $A_{12}$, $A_{22}$, and $A_{32}$ are independently monovalent aromatic ring residues, alkyl groups or hydrogen atoms. The aromatic ring residues may have a fused ring and is any of monovalent residues of aromatic hydrocarbon rings and aromatic heterocyclic rings, for example, benzene, naphthalene, anthracene, pyrene, etc.; thiophene; furan; pyrrole; and biphenyl. Often these residues are identical although they may be different. The aromatic rings may have a substituent or substituents, for example, alkyl groups preferably having 1 to 8 carbon atoms, aryl groups preferably having 6 to 15 carbon atoms, alkoxy and aryloxy groups having said alkyl and aryl groups, aralkyl and alkaryl groups having said alkyl and aryl groups, primary to tertiary amino groups which may have said alkyl and aryl groups, cyano groups, nitro groups, and halogen atoms.

The alkyl groups represented by $A_{12}$, $A_{22}$, and $A_{32}$ may be either linear or branched. Alkyl groups having 1 to 8 carbon atoms, especially 1 to 6 carbon atoms are preferred. They may have an aryl group, especially phenyl as a substituent.

The inventive compounds are characterized by the presence of an amino group —$N\Phi_{01}\Phi_{02}$, —$NH\Phi_{01}$ or —$NR_{01}\Phi_{01}$ at the branch terminal. It is only required that one amino group is present in a molecule as $R_{11}$ to $R_{31}$ although the inclusion of two, especially three amino groups is preferred. Since $A_{12}$ to $A_{32}$ can be aromatic ring residues $\Phi_{12}$ to $\Phi_{32}$ which may have —$N\Phi_{01}\Phi_{02}$, —$NH\Phi_{01}$ or —$NR_{01}\Phi_{01}$ as a substituent, it is preferred that three to six amino groups are present in a molecule. Preferred examples of the amino group are as mentioned above.

The compounds of the invention can be synthesized by a method as disclosed in W. Ishikawa, H. Inada, H. Nakano and Y. Shirota, Chem. Lett., 1991, 1731–1734, W. Ishikawa, H. Inada, H. Nakano and Y. Shirota, Mol. Cryst. Liq. Cryst., 211 (1992), 431–438, W. Ishikawa, H. Inada, H. Nakano and Y. Shirota, J. Phys. D., and J. Appl. Phys., 26, B94–B99 (1993). More particularly, Ullmann reaction is effected between a compound of formula (VI) such as 1,3,5-tris[(4-diphenylaminophenyl)amino[benzene and a compound of formula (VII) such as iodobenzene or an iodide such as alkyl iodides.

(VI)

$R_{12}\Phi_{12}I$ (VII)

Illustrative examples of the compound of formula (I) are listed in Table 1 as Compound Nos. 1 to 20.

TABLE 1

| Compound No. | $\phi_{11}, \phi_{21}, \phi_{31}$ | $R_{11}, R_{21}, R_{31}$ | $A_{12}, A_{22}, A_{32}$ |
|---|---|---|---|
| 1 | ⟨phenylene⟩ | —N(phenyl)(phenyl) | ⟨phenyl⟩ |

TABLE 1-continued

| Compound No. | $\phi_{11}, \phi_{21}, \phi_{31}$ | $R_{11}, R_{21}, R_{31}$ | $A_{12}, A_{22}, A_{32}$ |
|---|---|---|---|
| 2 |  |  |  |
| 3 |  |  |  |
| 4 |  |  |  |
| 5 |  |  |  |
| 6 |  |  |  |
| 7 |  |  |  |
| 8 |  |  |  |

TABLE 1-continued

| Compound No. | φ₁₁, φ₂₁, φ₃₁ | R₁₁, R₂₁, R₃₁ | A₁₂, A₂₂, A₃₂ |
| --- | --- | --- | --- |
| 9 | -C₆H₄- | -N(C₆H₅)₂ | 1-naphthyl |
| 10 | -C₆H₄- | -N(C₆H₅)₂ | anthracenyl |
| 11 | -C₆H₄- | -N(C₆H₅)₂ | pyrenyl |
| 12 | -C₆H₄- | -NH(C₆H₅) | phenyl |
| 13 | -C₆H₄- | -N(CH₃)(C₆H₅) | phenyl |
| 14 | -C₆H₄- | -N(C₆H₅)₂ | -CH₃ |
| 15 | -C₆H₄- | -N(C₆H₅)₂ | -C₂H₅ |

TABLE 1-continued

| Compound No. | $\phi_{11}, \phi_{21}, \phi_{31}$ | $R_{11}, R_{21}, R_{31}$ | $A_{12}, A_{22}, A_{32}$ |
|---|---|---|---|
| 16 |  | | $-C_3H_7$ |
| 17 |  | | $-C_6H_{13}$ |
| 18 |  | | $-CH_2-\underset{\underset{CH_3}{\mid}}{CH}-CH_3$ |
| 19 |  | | $-CH_2-\phenyl$ |
| 20 |  | | H |

The compounds of the invention have a molecular weight of about 500 to 3,000, a high melting point of 100° to 300° C., and Tg of 30° to 200° C., especially 80° to 200° C. By vacuum evaporation or other conventional techniques, the compounds can be deposited to form transparent and smooth films which maintain a stable amorphous state above room temperature. Such excellent film quality lasts long.

Figure 1:
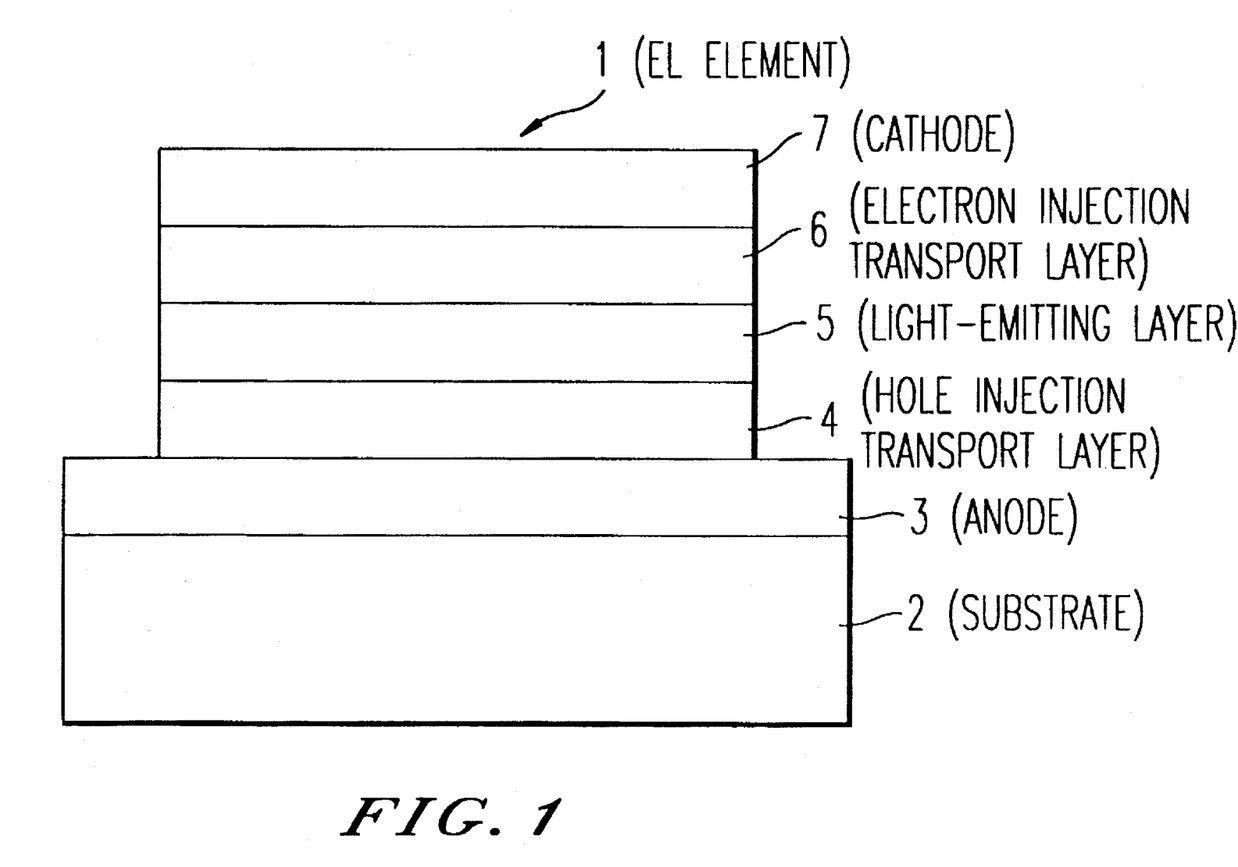
FIG. 1 is a side elevation of one exemplary structure of an EL element according to the present invention.

The EL element of the invention includes at least one organic compound layer. The organic compound layer or at least one of organic compound layers contains the inventive compound. One exemplary structure of the EL element according to the present invention is shown in FIG. 1. The EL element generally designated at 1 in FIG. 1 includes on a substrate 2, an anode 3, a hole injection transport layer 4, a light emitting layer 5, an electron injection transport layer 6, and a cathode 7 stacked in the described order from bottom to top.

The light emitting layer has multi-functions of injecting holes and electrons, transporting them, and recombining holes and electrons to create excitons. The hole injection transport layer has functions of facilitating injection of holes from the anode, transporting them, and obstructing electrons. The electron injection transport layer has functions of facilitating injection of electrons from the cathode and transporting them. These two layers are effective for increasing the number of holes and electrons injected into the light emitting layer to improve light emission efficacy. Therefore the hole and electron injection transport layers are optionally provided by taking into account the magnitude of the respective functions of the compound used in the light emitting layer for electron injection and transport, hole injection and transport. For example, if the compound used in the light emitting layer has an enhanced hole or electron injection transport function, the hole or electron injection transport layer may be omitted because the light emitting layer itself can also serve as a hole or electron injection transport layer. In some cases, both the hole and electron injection transport layers may be omitted.

The compound of the invention has good hole injection transport capability and is thus preferably used in the electron injection transport layer. Therefore, the following description is made to the embodiment wherein the compound of the invention is mused in the electron injection transport layer. Then the light emitting layer contains a luminescent substance. The luminescent substance may be selected from compounds as disclosed in JP-A 264692/1988, for example, coumarin, quinacridone, rubrene, and styryl series dyes alone or in admixture. Typical examples are tetraphenylbutadiene, anthracene, perylene, coronene, 12-phthaloperinone derivatives, and tris(8-quinolinol)aluminum. For example, a light emitting layer of a desired thickness may be formed by evaporating the organic luminescent substance or by coating a dispersion of the organic luminescent substance in a resin binder.

The compound of the invention is used in the hole injection transport layer. The layer may be formed by evaporating or coating the compound. A satisfactory amorphous film is obtained by evaporation. In combination with the inventive compound used in the hole injection transport layer, any of various other organic compounds used in conventional organic EL elements, for example, the organic compounds described in JP-A 295695/1988, 191694/1990, and 000792/1991 may be used additionally in the hole injection transport layer or as the electron injection transport layer. For example, in the hole injection transport layer, any of aromatic tertiary amines, hydrazone derivatives and carbazole derivatives may be laminated or mixed in an amount of less than 10 mol % with the compound of the invention. In the case of lamination, the inventive compound is desirably interposed between the anode and the additional hole injection transport layer. For the electron injection transport layer, oxadiazole derivatives may be used.

The organic compound layer may further contain a singlet oxygen quencher. Exemplary quenchers include nickel complexes, rubrene, diphenylisobenzofuran, and tertiary amines, with the rubrene being preferred. Such a quencher is preferably present in an amount of up to 10 mol % based on the moles of the inventive compound.

The thicknesses of the light emitting layer, hole and electron injection transport layers are not critical and vary with a particular formation technique. Preferably the light emitting layer has a thickness in the range of about 10 to 1,000 nm, especially about 50 to 200 nm. The hole and electron injection transport layers may have a thickness of the equivalent order to the light emitting layer.

The cathode is preferably made of a material having a low work function, for example, Li, Na, Mg, Al, Ag, In and alloys containing at least one of these elements. The cathode should preferably be of fine grains, especially amorphous. The cathode preferably has a thickness of about 10 to 1,000 nm.

In order that the EL element produce plane light emission, at least one of the electrodes should be transparent or semi-transparent. Since the material of the cathode is limited as mentioned just above, it is preferred to select the material and thickness of the anode so as to provide a transmittance of at least 80% to the emitted radiation. For example, the anode is preferably made of indium tin oxide (ITO), $SnO_2$, Ni, Au, Pt, Pd, polythiophene, and polypyrrole. The anode preferably has a thickness of about 10 to 500 nm.

The substrate may be made of any desired material although a transparent or semi-transparent material such as glass and resins is used in the illustrated embodiment wherein light exits from the substrate side. Where the substrate is made of an opaque material, the layer stacking order may be reversed from that shown in FIG. 1.

Next, it is described how to prepare the EL element of the present invention. The cathode and anode are preferably formed by gas phase deposition techniques such as vacuum evaporation and sputtering. The light emitting layer and hole and electron injection transport layers are preferably formed by vacuum evaporation because homogeneous amorphous thin films are available.

The conditions for vacuum evaporation are not critical although a vacuum of up to $10^{-3}$ Pa and an evaporation rate of about 0.1 to 1 nm/sec. are preferred. It is preferred to successively form the respective layers in vacuum because the successive formation in vacuum can avoid adsorption of impurities at the interface between the layers, thus ensuring high quality and a lower voltage for driving the element. In the embodiment wherein the respective layers are formed by vacuum evaporation, where it is desired for a single layer to contain two or more compounds, boats having the compounds received therein are individually temperature controlled to achieve co-deposition. Alternatively, a premix of the respective compounds is subject to evaporation. Also employable are solution coating techniques such as spin coating, dipping and casting and Langmuir-Blodgett's technique. For the solution coating, the compound of the invention may be dispersed in a matrix substance such as a polymer.

The EL element of the invention is generally of the DC drive type while it can be of the AC or pulse drive type. The applied voltage is generally about 3 to 20 volts.

EXAMPLE

Examples of the present invention are given below by way of illustration and not by way of limitation.

EXAMPLE 1

Compound No. 1 in Table 1 was synthesized by the following reaction scheme.

-continued

First, a 50-ml three necked flask was charged with 10.4 grams (0.04 mol) of 4-diphenylaminobenzene, 1.26 grams (0.01 mol) of trihydroxybenzene, and 0.2 grams (0.0008 mol) of iodine in a nitrogen atmosphere. Reaction was effected at 190° C. for 6 hours to form 1,3,5-tris[N-(4-diphenylaminophenyl)amino]benzene. After the completion of reaction, the reaction product was extracted with hot benzene. After the benzene was distilled off, the product was isolated and purified by silica gel column chromatography using benzene as a developer.

A 50-ml three necked flask was charged with 2.13 grams (0.0025 mol) of the resulting 1,3,5-tris[N-(4-diphenylaminophenyl)amino[benzene, 1.04 grams (0.02 mol) of iodobenzene, 2.24 grams (0.04 mol) of KOH, 1 gram of copper, and 3 ml of decalin in a nitrogen atmosphere. Ullmann reaction was carried out at 170° C. for 14 hours. After the completion of reaction, the reaction product was extracted with hot benzene. The product was isolated by silica gel column chromatography using benzene/hexane as a developer and recrystallized from benzene/hexane for purification. The yield was 1.75 grams, 65%. On analysis by IR, NMR, mass analysis, and elemental analysis, the product was identified to be Compound No. 1.

Figure 2:
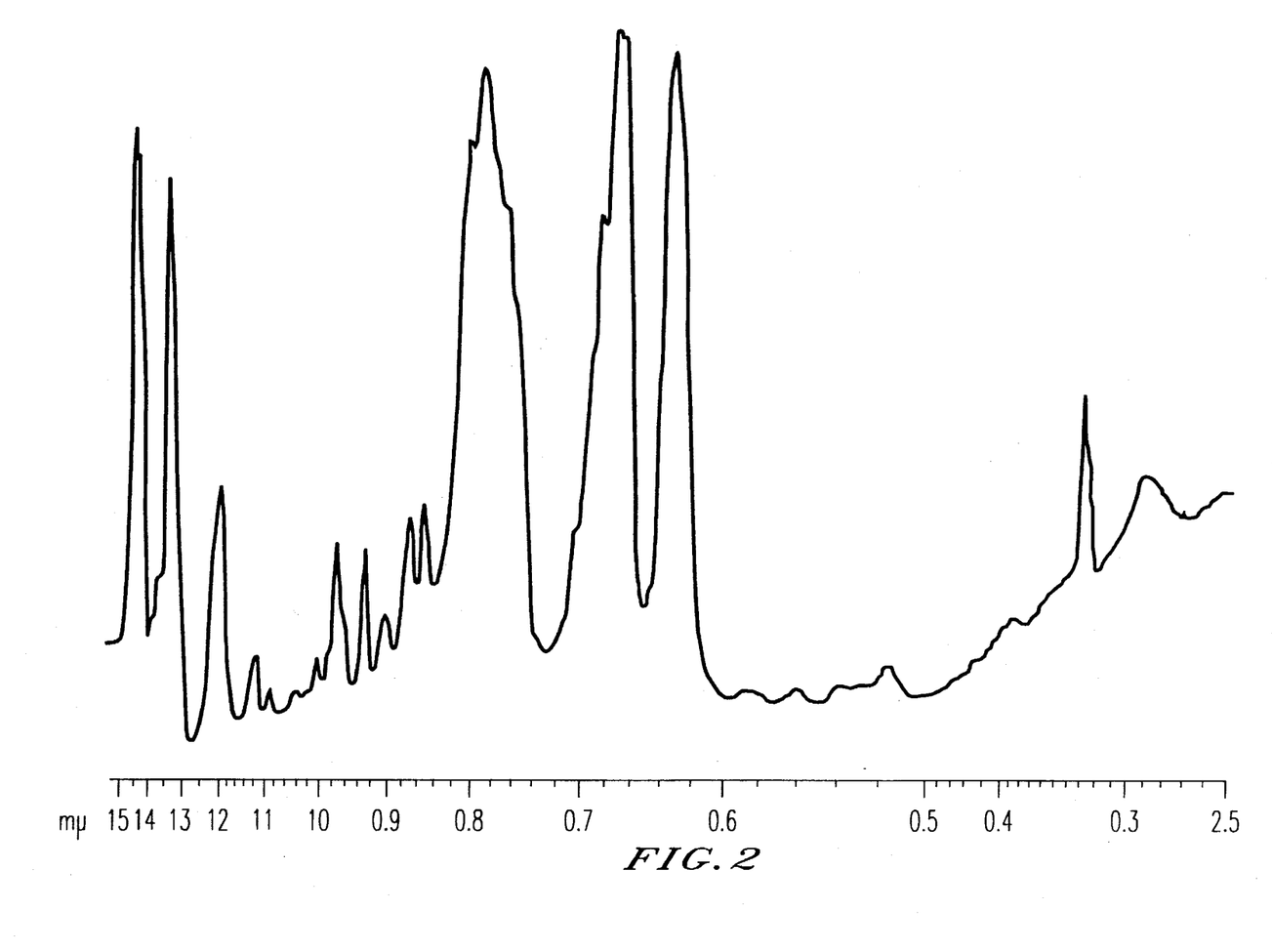
FIG. 2 is an infrared absorption spectrum of Compound No. 1.

IR spectrum: shown in FIG. 2. UV: (λmax, logε) (310 nm, 4.85) proton-NMR: 6.3 to 6.8 Mass analysis: m/e 1080 (M+)

| Elemental analysis: | | | |
|---|---|---|---|
| | C | H | N |
| Calcd. (%) | 86.64 | 5.59 | 7.77 |
| Found (%) | 86.90 | 5.63 | 7.74 |

Figure 3:
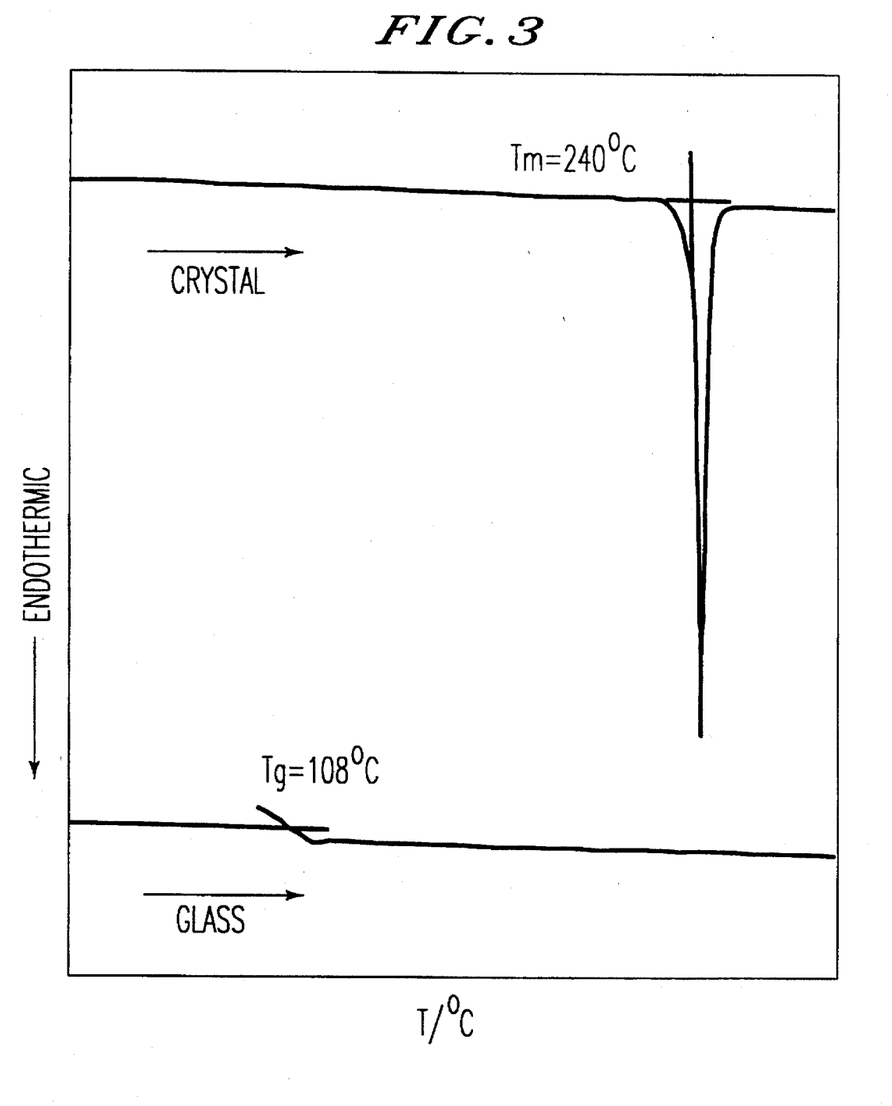
FIG. 3 is a DSC diagram of Compound No. 1.

Differential scanning calorimetry (DSC): shown in FIG. 3. Melting point: 240° C. Tg: 108° C.

EXAMPLE 2

A glass substrate having an ITO transparent electrode (anode) of 200 nm thick thereon was cleaned by ultrasonic scrubbing in neutral detergent, acetone and then ethanol. The substrate was pulled up from boiling ethanol, dried and rested on a holder in an evaporation chamber which was evacuated to a vacuum of $8 \times 10^{-5}$ Pa.

Compound No. 1 was evaporated and deposited to a thickness of 50 nm at a rate of 0.2 nm/sec., obtaining a hole injection transport layer. While the chamber was kept vacuum, tris(8-quinolinol)aluminum was evaporated and deposited to a thickness of 50 nm at a rate of 0.2 nm/sec., obtaining a light emitting layer having an enhanced electron injection transport function. While the chamber was still kept vacuum, a metal mix of Mg and Ag in a weight ratio of 10:1 was evaporated and deposited to a thickness of 200 nm at a rate of 0.2 nm/sec., obtaining a cathode. An EL element was produced in this way.

Figure 4:
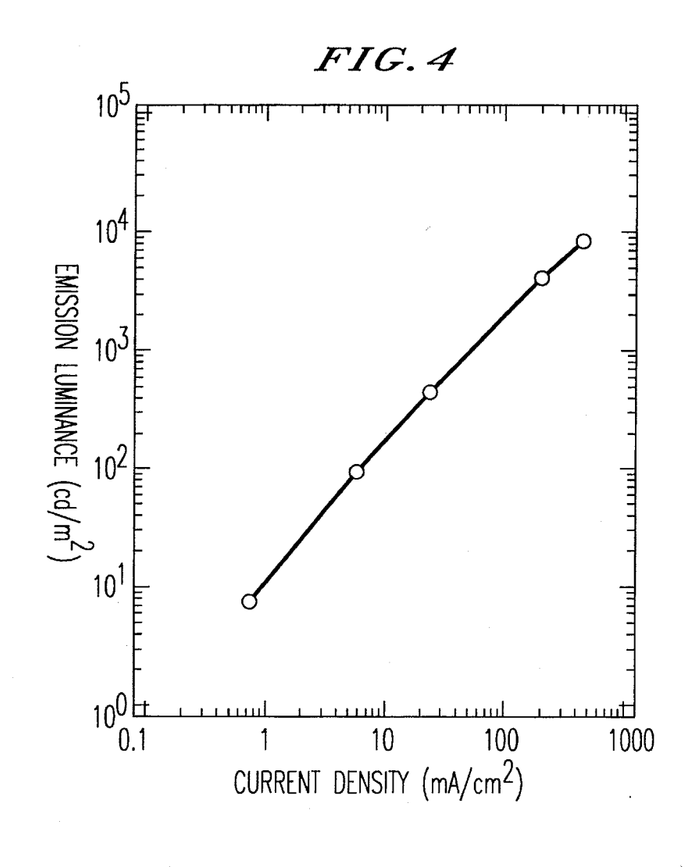
FIG. 4 is a diagram showing luminance vs. current density of the EL element of Example 2.
Figure 5:
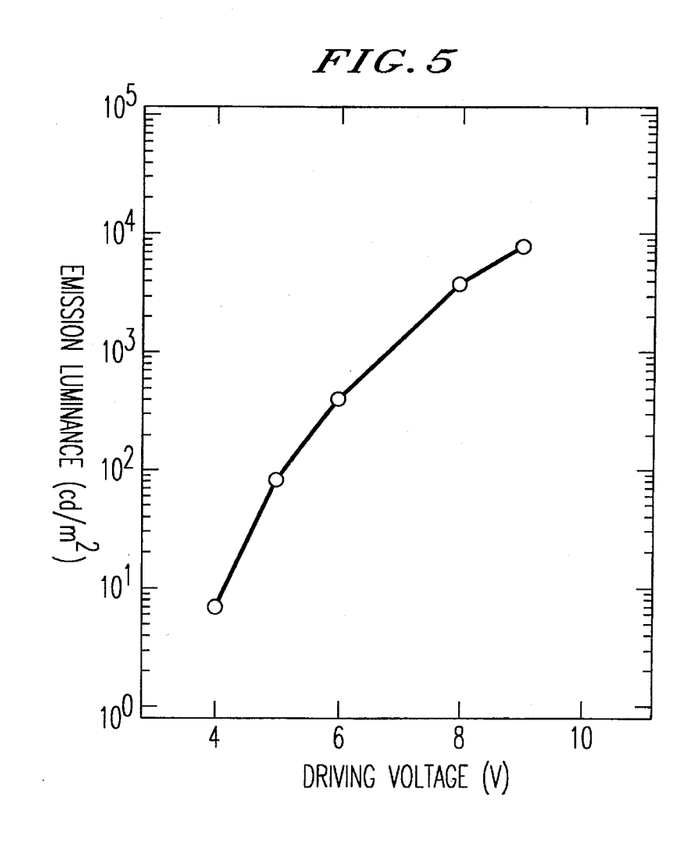
FIG. 5 is a diagram showing luminance vs. driving voltage of the EL element of Example 2.

The EL element was operated for light emission by applying voltage. FIG. 4 shows the luminance as a function of current density. FIG. 5 shows the luminance as a function of drive voltage. Emission of yellowish green light (light emission maximum wavelength λmax=495 nm) was observed.

The threshold current density immediately before breakdown was 1,500 mA/cm$^2$, which was approximately twice the conventional value, indicating improved durability.

Figure 6A:
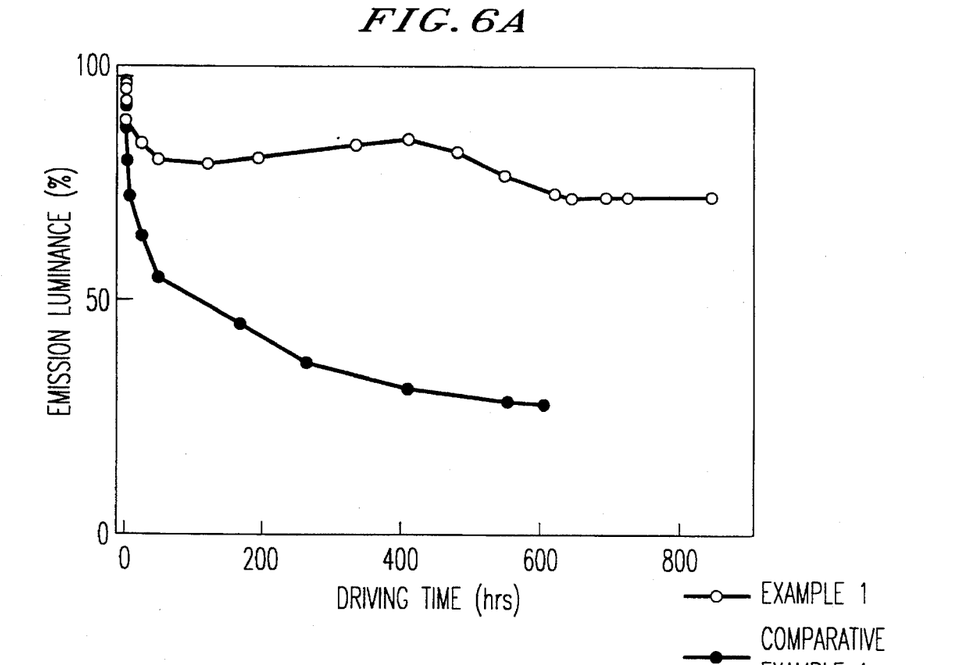
FIG. 6 includes graphs of luminance and driving voltage vs. driving time of the compounds of Example 1 and Comparative Example 1, for comparing their continuous operation stability.
Figure 6B:
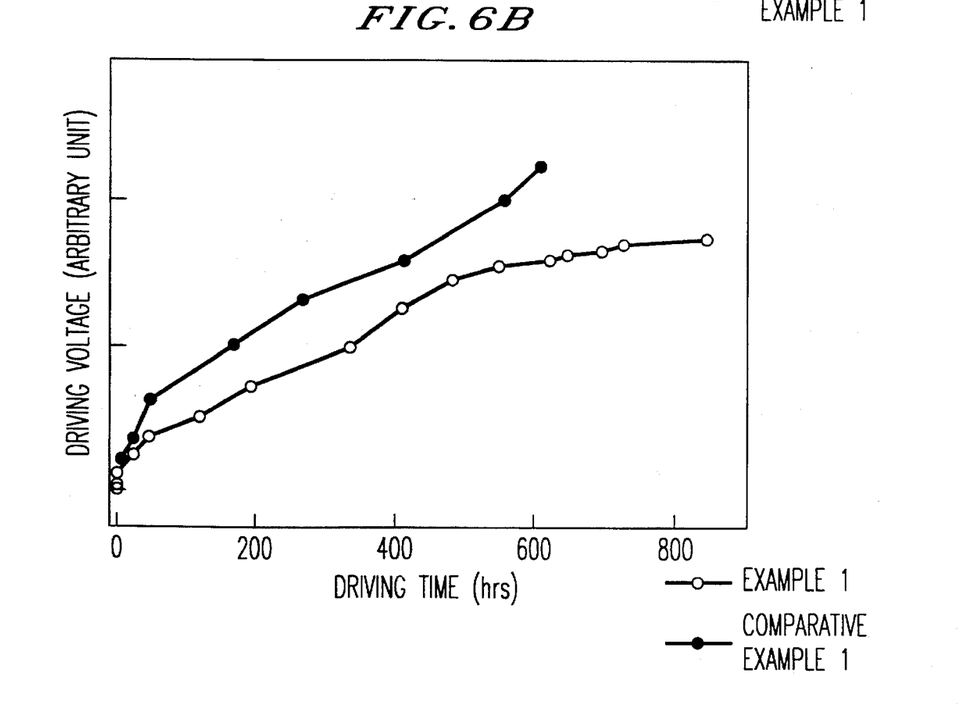

The EL element was continuously operated at a constant current density of 10 mA/cm$^2$ by applying DC voltage. The emission luminance was 170 cd/m$^2$ at a drive voltage of 5.3 volts at the initial and remained above the practical luminance level of 100 cd/m$^2$ after 800 hours because the attenuation was as little as 30%. The driving voltage increased only a little, indicating good driving stability. The changes of luminance and driving voltage with time are shown in FIG. 6.

COMPARATIVE EXAMPLE 1

An EL element was fabricated by the same procedure as in Example 2 except that N,N'-diphenyl-di(3-methylphenyl)-4,4'-diaminobiphenyl (TPD) was used instead of Compound No. 1. Note that TPD had a melting point of 171.2° C. and a Tg of 61.3° C. This EL element was continuously operated as in Example 2. The emission luminance was 340 cd/m$^2$ at a drive voltage of 6.1 volts at the initial, but lowered to one half after 100 hours and attenuated to below 100 cd/m$^2$ after 300 hours. The driving voltage markedly increased and the element was broken at 670 hours of operation. The changes of luminance and driving voltage with time are also shown in FIG. 6.

COMPARATIVE EXAMPLE 2

An EL element was fabricated by the same procedure as in Example 2 except that 4,4',4"-tris(diphenylamino)triphenylamine (TDATA) was used instead of Compound No. 1. On DSC analysis, TDATA had a melting point of 239° C., a Tg of 89° C., a crystallization point of 130° C. A vitreous film was formed by quenching the film with liquefied nitrogen because the film did not become vitreous when it was allowed to cool down. Immediately after removal from the evaporation chamber, some EL elements crystallized and became white turbid. Only those EL elements which did not become white turbid were continuously operated as in Example 2. The elements experienced a half loss of emission luminance after 6 hours of operation and dielectric breakdown next day.

A comparison of Example 2 with Comparative Examples 1 and 2 reveals the effectiveness of the invention.

EXAMPLE 3

Compound Nos. 2 to 13 were synthesized by Ullmann reaction as in Example 1. They were identified by IR, NMR, mass analysis, and elemental analysis as in Example 1. Using these compounds, El elements were fabricated and tested as in Example 2, obtaining equivalent results.

EXAMPLE 4

Compound Nos. 14 to 19 were obtained by the same procedure as in Example 1 except that the iodobenzene was replaced by corresponding alkyl iodides. The reaction temperature was 40° to 170° C. and the time was 5 to 20 hours. They were identified by IR, NMR, mass analysis, and elemental analysis. When fabricated into EL elements, they also provided equivalent results to Example 2.

EXAMPLE 5

Using Compound No. 20 which is an intermediate compound in Example 1, an EL element was fabricated, with equivalent results to Example 2.

The compounds of the invention have high mp and high Tg. They form transparent smooth films capable of maintaining a stable amorphous state even above room temperature, that is, of acceptable quality. The EL element of the invention which uses the compound in an organic compound layer, especially in a hole injection transport layer produces uniform plane light emission, maintains high luminance over a long period of time, and is thus durable.

In addition to organic EL elements, the compounds of the invention are applicable as organic semiconductor substances having donor property in photo-electric conversion elements such as photo-cells and photo-sensors. They are also useful as thermochromic substances utilizing transition between amorphous and crystalline states.

Although some preferred embodiments have been described, many modifications and variations may be made thereto in the light of the above teachings. It is therefore to be understood that within the scope of the appended claims, the invention may be practiced otherwise than as specifically described.

We claim:

1. A trisarylaminobenzene derivative of the following formula:

(I)

wherein $\Phi_{11}$, $\Phi_{21}$, and $\Phi_{31}$ are independently divalent aromatic ring residues, $R_{11}$, $R_{21}$, and $R_{31}$ are independently selected from groups represented by —N$\Phi_{01}\Phi_{02}$, —NH$\Phi_{01}$, —NR$_{01}\Phi_{01}$, —$\Phi_{01}$, —O$\Phi_{01}$ and —S$\Phi_{01}$ wherein each of $\Phi_{01}$ and $\Phi_{02}$ is a monovalent aromatic ring residue, and $R_{01}$ is an alkyl group, at least one of $R_{11}$, $R_{21}$, and $R_{31}$ being a group represented by —N$\Phi_{01}\Phi_{02}$, —NH$\Phi_{01}$ or —NR$_{01}\Phi_{01}$, and $A_{12}$, $A_{22}$, and $A_{32}$ are independently monovalent aromatic ring residues, alkyl groups or hydrogen atoms.

2. A trisarylaminobenzene derivative according to claim 1 wherein each of $R_{11}$, $R_{21}$, and $R_{31}$ is a group represented by —N$\Phi_{01}\Phi_{02}$, —NH$\Phi_{01}$ or —NR$_{01}\Phi_{01}$.

3. A trisarylaminobenzene derivative according to claim 2 which is of the following formula:

(II)

wherein $\Phi_{11}$, $\Phi_{21}$, $\Phi_{31}$, $\Phi_{01}$, and $\Phi_{02}$ are as defined in formula (I), the three $\Phi_{01}$ groups may be identical or different and the three $\Phi_{02}$ groups may be identical or different, and $\Phi_{12}$, $\Phi_{22}$, and $\Phi_{32}$ are independently monovalent aromatic ring residues.

4. A trisarylaminobenzene derivative according to claim 3 which is of the following formula:

(III)

wherein $R_1$ and $R_2$ groups, nine in total, may be identical or different and each selected from the group consisting of a hydrogen atom, halogen atom, alkyl group, aryl group, alkoxy group, aryloxy group, aralkyl group, alkaryl group, primary to tertiary amino group, cyano group, and nitro group.

5. A trisarylaminobenzene derivative according to claim 2 which is of the following formula:

(IV)

wherein $\Phi_{11}$, $\Phi_{21}$, $\Phi_{31}$, $\Phi_{01}$, and $\Phi_{02}$ are as defined in formula (I), the three $\Phi_{01}$ groups may be identical or different and the three $\Phi_{02}$ groups may be identical or different, and $R_{12}$, $R_{22}$, and $R_{32}$ are independently alkyl groups or hydrogen atoms.

6. A trisarylaminobenzene derivative according to claim 5 which is of the following formula:

(V)

wherein R groups, six in total, may be identical or different and each selected from the group consisting of a hydrogen atom, halogen atom, alkyl group, aryl group, alkoxy group, aryloxy group, aralkyl group, alkaryl group, primary to tertiary amino group, cyano group, and nitro group, and $R_{12}$, $R_{22}$, and $R_{32}$ are as defined in formula (IV).

7. A compound for use in an organic electroluminescent element which is a trisarylaminobenzene derivative according to any one of claims 1 to 6.

8. An organic electroluminescent element comprising a layer containing a trisarylaminobenzene compound of the following formula:

wherein $\Phi_{11}$, $\Phi_{21}$, and $\Phi_{31}$ are independently divalent aromatic ring residues, $R_{11}$, $R_{21}$, and $R_{31}$ are independently selected from groups represented by —$N\Phi_{01}\Phi_{02}$, —$NH\Phi_{01}$, —$NR_{01}\Phi_{01}$, —$\Phi_{01}$, —$O\Phi_{01}$ and $S\Phi_{01}$ wherein each of $\Phi_{01}$ and $\Phi_{02}$ is a monovalent aromatic ring residue, and $R_{01}$ is an alkyl group, at least one of $R_{11}$, $R_{21}$, and $R_{31}$ being a group represented by —$N\Phi_{01}\Phi_{02}$, —$NH\Phi_{01}$ or —$NR_{01}\Phi_{01}$, and $A_{12}$, $A_{22}$, and $A_{32}$ are independently monovalent aromatic ring residues, alkyl groups or hydrogen atoms.

9. An organic electroluminescent element according to claim 8 which comprises a hole injection transport layer containing said compound and a light emitting layer.

10. An organic electroluminescent element according to claim 9 which further comprises an electron injection transport layer.

* * * * *